United States Patent [19]
Murase

[11] Patent Number: 4,917,098
[45] Date of Patent: Apr. 17, 1990

[54] METHOD AND APPARATUS FOR MEASURING BLOOD PRESSURE

[75] Inventor: Tadashi Murase, Gifu, Japan

[73] Assignee: Colin Electronics Co., Ltd., Aichi, Japan

[21] Appl. No.: 314,096

[22] Filed: Feb. 23, 1989

[51] Int. Cl.⁴ .............................................. A61B 5/02
[52] U.S. Cl. ..................................... 128/677; 128/681
[58] Field of Search ..................... 128/672, 677–686, 128/687–690

[56] References Cited

U.S. PATENT DOCUMENTS

| | | | |
|---|---|---|---|
| 4,262,675 | 4/1981 | Kubo et al. | 128/680 |
| 4,427,013 | 1/1984 | Nunn et al. | 128/681 |
| 4,796,184 | 1/1989 | Bahr et al. | 128/682 X |
| 4,799,492 | 1/1989 | Nelson | 128/677 X |
| 4,830,019 | 5/1989 | Shirasaki et al. | 128/680 X |

*Primary Examiner*—Angela D. Sykes
*Attorney, Agent, or Firm*—Oliff & Berridge

[57] ABSTRACT

A method and an apparatus for determining blood pressure of a subject based on heartbeat-synchronous pulses, the method including the steps of detecting the heartbeat-synchronous pulses as pressure in an inflatable cuff set on a body portion of a subject is varied, preparing a plural sets of point data each of which represents a pressure of the cuff at the time of detection of a corresponding one of the pulses and a magnitude of the corresponding one pulse, plotting, based on the prepared plural sets of point data, a plurality of points in a two-dimensional table defined by a first axis indicative of the pressure of the cuff and a second axis indicative of the magnitude of the pulses, selecting a predetermined number of consecutive points from the plotted points such that the predetermined number is not less than three, determining a regression line of the selected consecutive points, such that each of the at least one point is plotted with a statistically high probability inside a corresponding one of the at least one prediction interval, and determining blood pressure of the subject based on the at least one point, if the each of the at least one point is plotted outside the corresponding one of the at least one prediction interval.

13 Claims, 9 Drawing Sheets

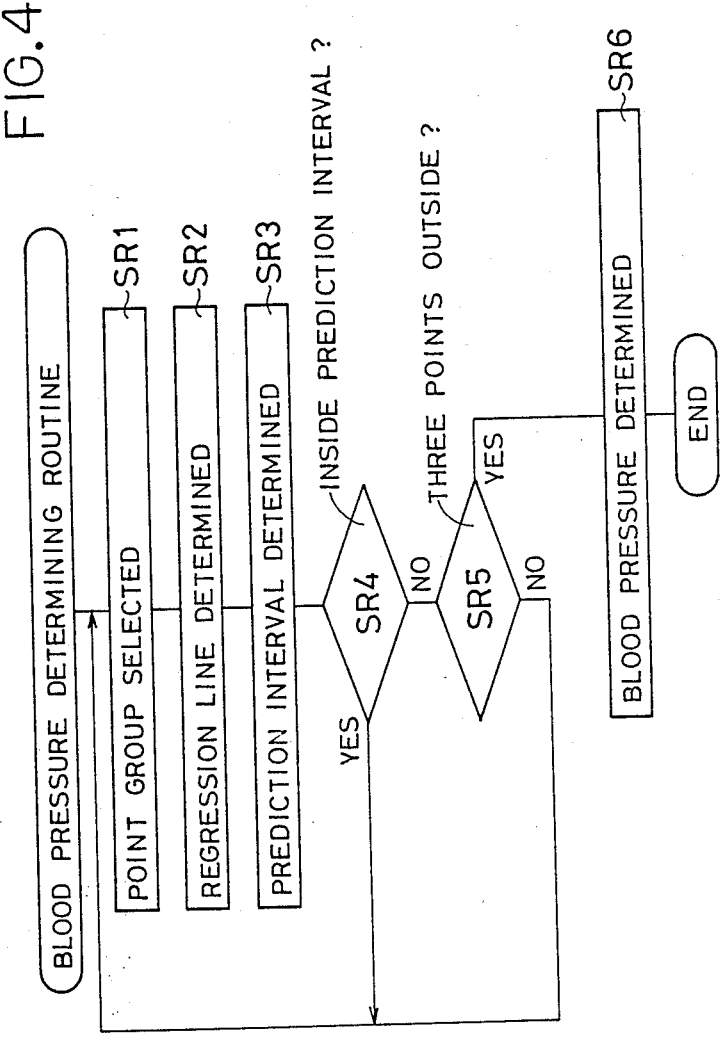

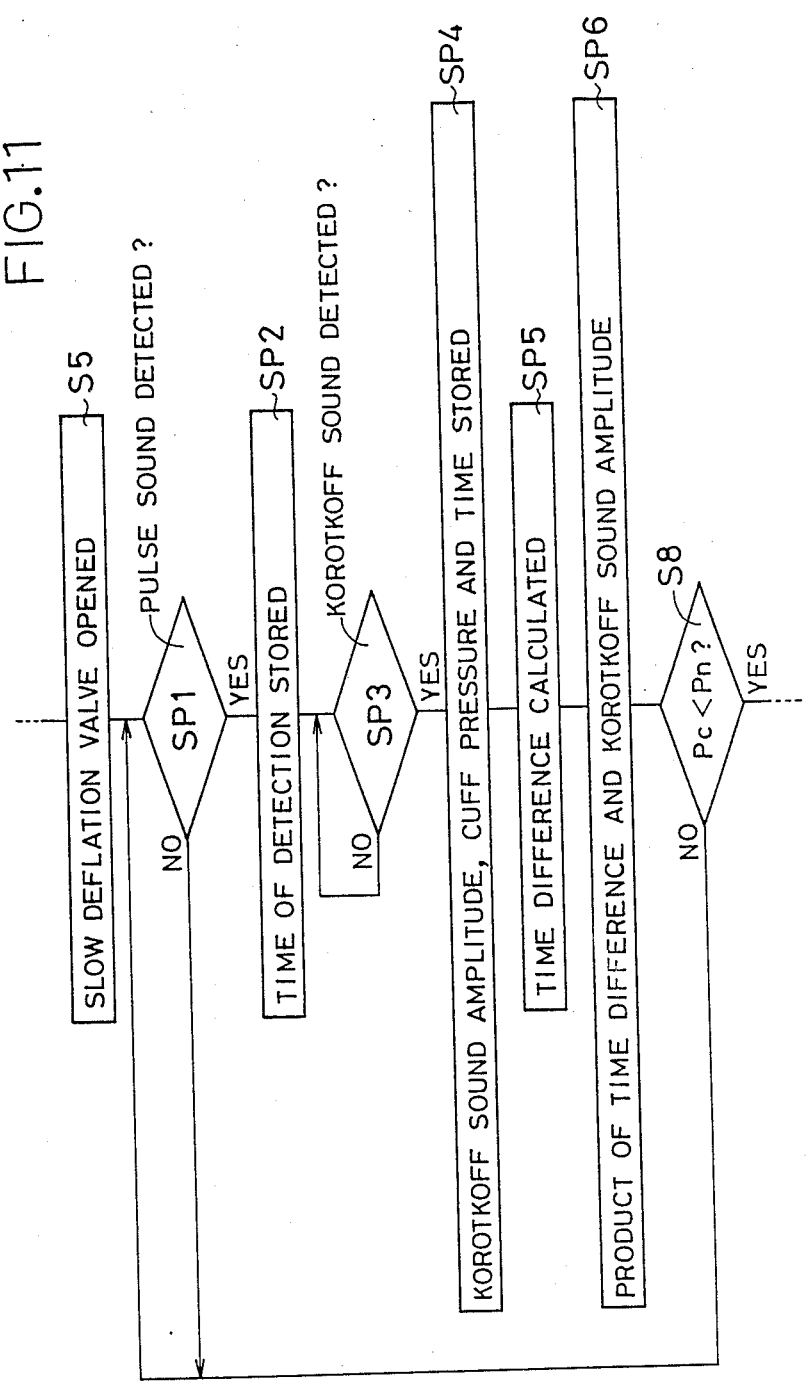

METHOD AND APPARATUS FOR MEASURING BLOOD PRESSURE

BACKGROUND OF THE INVENTION

1. Field of the Invention

The present invention relates to a method and an apparatus for determining blood pressure of a living body based on sets of data each of which represents a magnitude of a heartbeat-synchronous pulse and a cuff pressure at the time of detection of the pulse.

2. Discussion of the Prior Art

There are known various methods of automatically measuring blood pressue of a living body or subject as pressure in an inflatable cuff set on a body member of the subject is varied, such as (a) "Korotkoff sounds" method in which Korotkoff sounds are detected and blood pressure is determined based on variation in magnitude of the detected Korotkoff sounds; (b) "oscillometric" method in which pressure oscillation transmitted to the cuff synchronously with heartbeat of the subject, namely, pulse wave is detected and blood pressure is determined based on magnitude variation of the detected pulse wave; and (c) "supersonic" method in which vibrations of the wall of an artery are detected by utilizing Doppler effect of supersonic wave and blood pressure is determined based on magnitude variation of the detected artery-wall vibrations.

In each of the above-indicated blood pressure measuring methods, are plotted points representing magnitudes of Korotkoff sounds, pulses of pulse wave or vibrations of artery wall that are heartbeat-synchronous pulses produced from the subject synchronously with heartbeat of the subject. The points are plotted along an axis indicative of pressure in the inflatable cuff (hereinafter, referred to as "cuff pressure"), and a blood pressure evaluation curve is obtained by connecting the plotted points. Blood pressure is automatically determined based on the thus obtained evaluation curve. For example, cuff pressure at the time the evaluation curve exceeds a predetermined magnitude or level, or at the time a difference in magnitude between each pair of adjacent two points becomes maximum, is determined as maximum or minimum blood pressure.

In the above-indicated conventional methods, if a smooth blood pressure evaluation curve were obtained blood pressure determined based on such curve would be accurate. However, generally it is difficult to obtain such smooth evaluation curve, because points representing the heartbeat-synchronous pulses are plotted with dispersion or variation due to various causes other than variation in cuff pressure. Therefore, the conventional methods suffer from the problem that the accuracy of blood pressure measurement is unsatisfactory.

SUMMARY OF THE INVENTION

It is therefore an object of the present invention to provide a method and an apparatus for determining blood pressure based on heartbeat-synchronous pulses, wherein the accuracy of blood pressure measurement is improved.

According to a first aspect of the present invention, there is provided a method of determining blood pressure of a subject based on heartbeat-synchronous pulses which are produced from the subject by pressing a body portion of the subject with an inflatable cuff, the method comprising the steps of (a) detecting the heartbeat-synchronous pulses as pressure in the cuff is varied, (b) preparing plural sets of point data each of which represents a pressure of the cuff at the time of detection of a correponding one of the pulses and a magnitude of the corresponding one pulse, (c) plotting, based on the prepared plural sets of point data, a plurality of points in a two-dimensional table defined by a first axis indicative of the pressure of the cuff and a second axis indicative of the magnitude of the pulses, (d) selecting a predetermined number of consecutive points from the plotted points such that the predetermined number is not less than three, (e) determining a regression line of the selected consecutive points, (f) statistically determining, based on the determined regression line, at least one prediction interval regarding at least one point adjacent to the selected consecutive points, such that each of the at least one point is plotted with a statistically high probability inside a corresponding one of the at least one prediction interval, and (g) determining blood pressure of the subject based on the at least one point, if the each of the at least one point is plotted outside the corresponding one of the at least one prediction interval.

In the blood pressure determining method arranged as described above, a varying or dispersing tendency of a predetermined number of consecutive points selected from the plotted points, are expressed as a regression line of the selected consecutive points, and a prediction interval regarding a point following or preceding the selected consecutive points, is statistically determined based on the regression line, such that the point in question is plotted with a statistically high probability inside the prediction interval, namely, such that, if the point has statistically the same varying tendency as that of the selected consecutive points, the point is plotted inside the prediction interval. Accordingly, if the point in question is plotted outside the prediction interval, it is statistically estimated that the point reflects a particular cause other than statistically predicted dispersion or variation. In this case, the point is determined as a special point, and cuff pressure represented by the special point or a point near the special point is determined as blood pressure of the subject. The thus determined blood pressure is sufficiently accurate.

In a preferred embodiment of the present invention, the method further comprises the steps of connecting the plotted points so as to obtain an evaluation curve, and determining, as a rising point of the evaluation curve, one of the at least one point if the each of the at least one point is plotted outside the corresponding one of the at least one prediction interval, a pressure of the cuff represented by the rising point being determined as the blood pressure of the subject.

In another embodiment of the method of the invention, the at least one prediction interval consists of three prediction intervals determined regarding three consecutive points adjacent to the selected consecutive points, a pressure of the cuff represented by one of the three consecutive points being determined as the blood pressure of the subject.

In yet another embodiment of the method of the invention, the heartbeat-synchronous pulses consist of pulses of pulse wave transmitted to the inflatable cuff synchronously with heartbeat of the subject. Alternatively, the heartbeat-synchronous pulses may consist of Korotkoff sounds produced from the body portion of the subject synchronously with heartbeat of the subject.

In a further embodiment of the method of the invention, the step of detecting the heartbeat-synchronous pulses is effected as the pressure of the inflatable cuff is decreased. In this case, the step of determining the blood pressure may consist of at least one of determining maximum blood pressure of the subject based on the at least one point following the selected consecutive points, and determining minimum blood pressure of the subject based on the at least one point preceding the selected consecutive points different from the selected points utilized in determining the maximum blood pressure.

In a still further embodiment of the method of the invention, the step of detecting the heartbeat-synchronous pulses is effected as the pressure of the inflatable cuff is increased. In this case, the step of determining the blood pressure may consist of at least one of determining minimum blood pressure of the subject based on the at least one point plotted following the selected consecutive points, and determining maximum blood pressure of the subject based on the at least one point preceding the selected consecutive points different from the selected points utilized in determining the minimum blood pressure.

According to a second aspect of the present invention, there is provided an apparatus for determining blood pressure of a subject based on heartbeat-synchronous pulses which are produced from the subject by pressing a body portion of the subject with an inflatable cuff, the apparatus comprising (1) means for detecting the heartbeat-synchronous pulses as pressure in the cuff is varied, (2) means for preparing plural sets of point data each of which represents a pressure of the cuff at the time of detection of a corresponding one of the pulses and a magnitude of the corresponding one pulse, and plotting, based on the prepared plural sets of point data, a plurality of points in a two-dimensional table defined by a first axis indicative of the pressure of the cuff and a second axis indicative of the magnitude of the pulses, (3) means for selecting a predetermined number of consecutive points from the plotted points such that the predetermined number is not less than three, and (4) means for determining a regression line of the selected consecutive points, (5) means for statistically determining, based on the determined regression line, at least one prediction interval regarding at least one point adjacent to the selected consecutive point, such that each of the at least one point is plotted with a statistically high probability inside a corresponding one of the at least one prediction interval, and (6) means for determining blood pressure of the subject based on the at least one point, if the each of the at least one point is plotted outside the corresponding one of the at least one prediction interval.

In a preferred embodiment of the apparatus of the present invention, the at least one prediction interval consists of three prediction intervals determined regarding three consecutive points adjacent to the selected consecutive points, a pressure of the cuff represented by one of the three consecutive points being determined as the blood pressure of the subject.

In another embodiment of the apparatus of the invention, the regression line is expressed by the following equation:

$$Y = aX + b,$$

wherein
X: pressure of the cuff,
Y: magnitude of the pulses,
a: slope (constant);

$$a = \frac{\Sigma(x - \bar{x})(y - \bar{y})}{\Sigma(x - \bar{x})}$$

b: y intercept (constant);

$$b = \bar{y} - a\bar{x}$$

x: pressure of the cuff represented by each of the selected consecutive points,
y: magnitude of the pulses represented by each of the selected consecutive points,
$\bar{x}$: average of the pressures of the cuff represented by the selected consecutive points, and
$\bar{y}$: average of the magnitudes of the pulses represented by the selected consecutive points.

In yet another embodiment of the apparatus of the invention, the prediction interval determined regarding a point P plotted adjacent to the selected consecutive points is is defined by an upper and a lower limit thereof which are expressed as follows:

$$a \cdot x_k + b \pm t_{\alpha/2} \cdot s \cdot \sqrt{1 + \frac{1}{n} + \frac{(x - \bar{x})^2}{\Sigma(x - \bar{x})^2}} \quad \frac{(x_K - \bar{x})^2}{\Sigma(x - \bar{x})^2}$$

wherein
$x_k$: x coordinate of the point P,
s: standard deviation of the selected consecutive points,
n: the predetermined number,
t: value from G-Distribution Table, and
α: significance level.

BRIEF DESCRIPTION OF THE DRAWINGS

The above and optional objects, features and advantages of the present invention will be better understood by reading the following detailed description of the presently preferred embodiments of the invention, when considered in conjunction with the accompanying drawings, in which:

FIG. 4 is a flow chart illustrating in detail a blood pressure determining routine effected in the flow chart of FIG. 2;

FIG. 11 is a flow chart illustrating a portion of the apparatus of FIG. 10.

DETAILED DESCRIPTION OF THE PREFERRED EMBODIMENT

Figure 1:
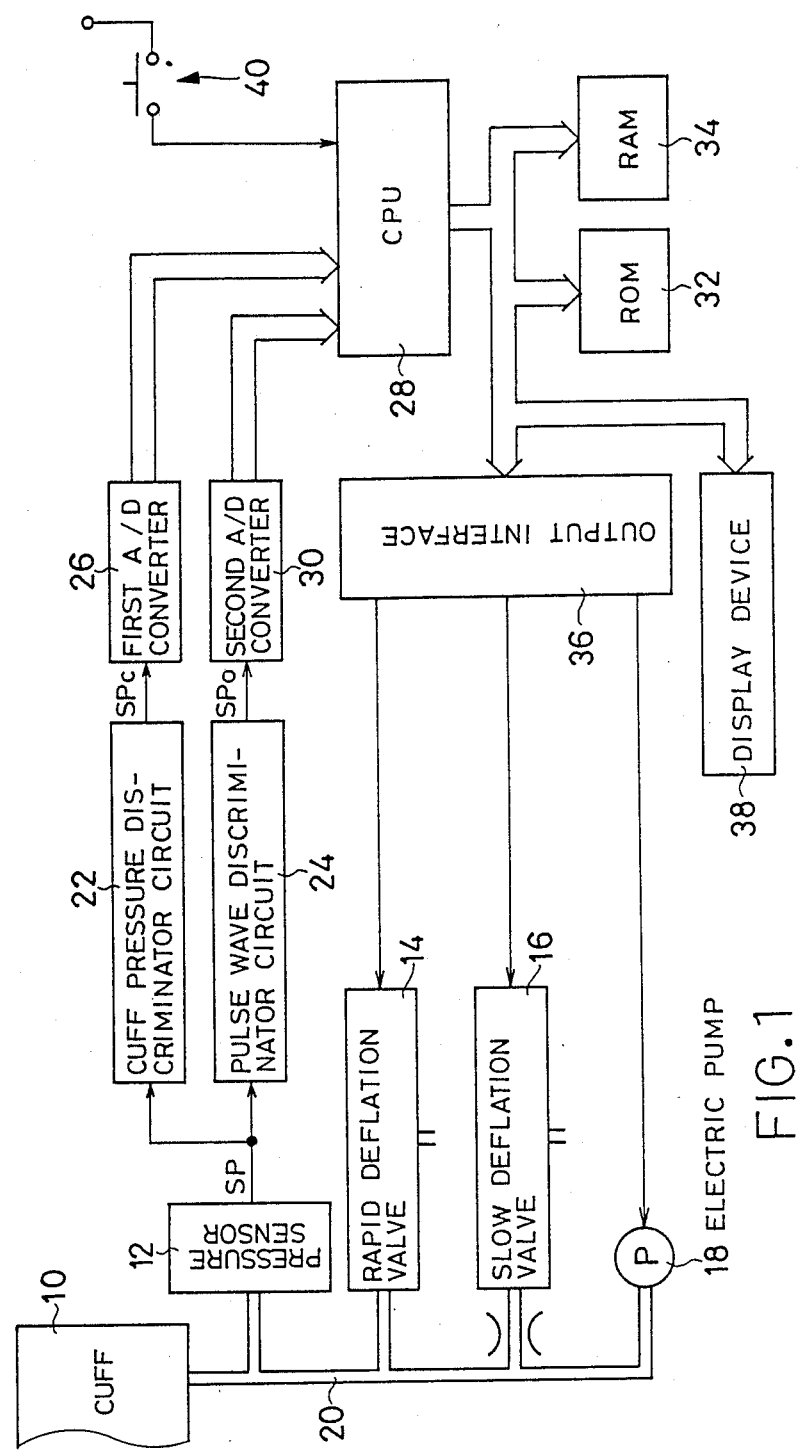
FIG. 1 is a diagrammatic view of a blood pressure measuring apparatus of the present invention.

Referring first to FIG. 1 there is shown a blood pressure measuring apparatus embodying the present invention. In the figure, reference numeral 10 designates an inflatable cuff. The cuff 10 has a bag-like structure, and is wound around an upper arm of a subject so as to press the arm upon being inflated. The cuff 10 is connected via piping 20 to a pressure sensor 12, a rapid deflation valve 14, a slow deflation valve 16 and an electrically operated pump 18. The pressure sensor 12 detects pressure in the cuff 10, and generates pressure signal SP representing the detected cuff pressure, to a cuff pressure discriminator circuit 22 and a pulse wave discriminator circuit 24. The cuff pressure discriminator circuit 22 includes a low-pass filter for discriminating, from pressure signal SP, signal SPc representing static pressure Pc in the cuff 10 (hereinafter, referred to as cuff pressure Pc), and supplies cuff pressure signal SPc to a CPU (central processing unit) 28 via a first A/D (analog-to-digital) converter 26. The pulse wave discriminator circuit 24 includes a band-pass filter for discriminating, from pressure signal SP, signal SPo representing dynamic pressure in the cuff 10, i.e., pressure oscillation transmitted to the cuff 10 from the upper arm of the subject. The pressure oscillation corresponds to pulses of pulse wave produced synchronously with heartbeat of the subject. Signal SPo consists of oscillometric signal representing pulses of the pulse wave. Pulse wave signal SPo transmitted through the pulse wave discriminator circuit 24 is supplied to the CPU 28 via a second A/D converter 30.

The CPU 28 cooperates with a ROM (read only memory) 32 and a RAM (random access memory) 34 to constitute a control device of the present blood pressure measuring apparatus. The CPU 28 processes the received signals according to programs pre-stored in the ROM 32 by utilizing temporary-storage function of the RAM 34, and generates drive signals to the rapid and slow deflation valves 14, 16 and electric pump 18 via an output interface 36. The CPU 28 also commands a display device 38 to display blood pressure of the subject.

Figure 2:
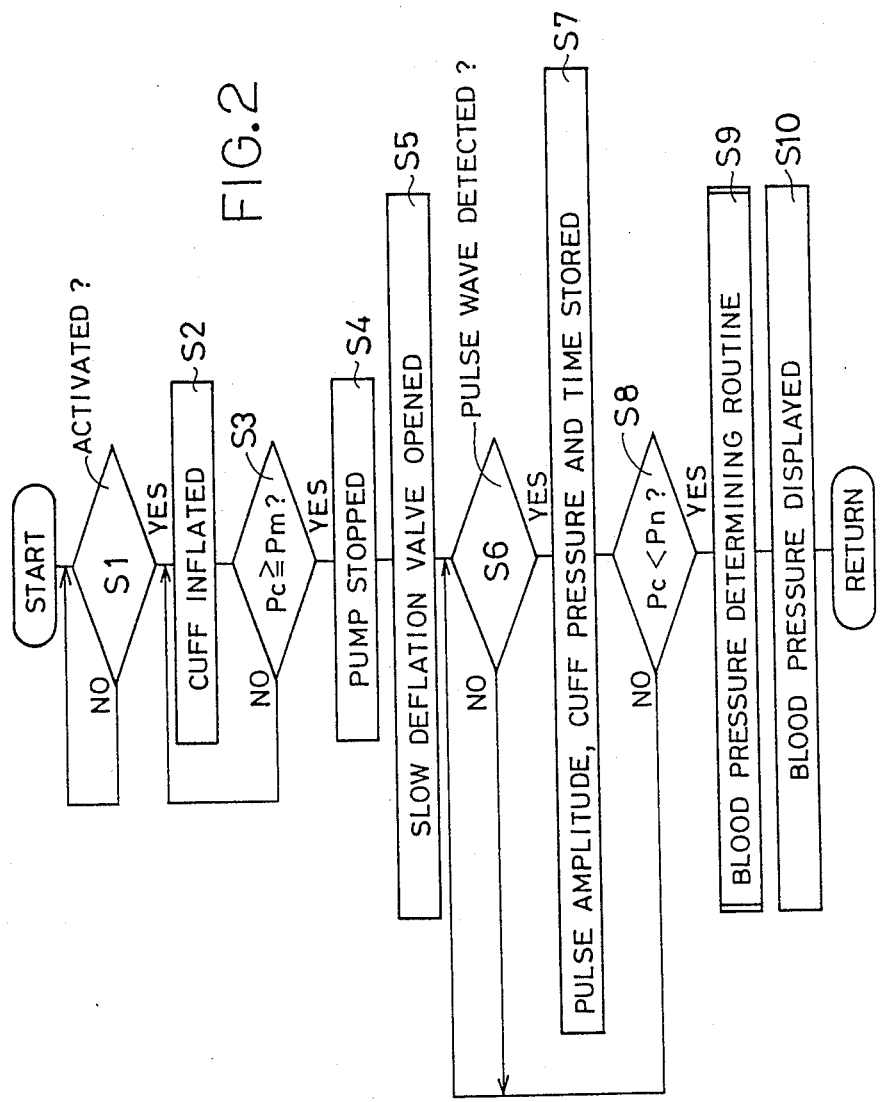
FIG. 2 is a flow chart illustrating the operation of the apparatus of FIG. 1.

Referring next to FIG. 2 there is illustrated the flow chart according to which the present apparatus is operated.

Initially at step S1, it is judged whether or not activation signal is present at the CPU 28. Activation signal is supplied to the CPU 28 from an ON/OFF switch 40 (FIG. 1) when the switch 40 is operated to activate the present apparatus, or from an activation circuit (not shown) at regular intervals of time to start respective blood pressure measurements. If the judgement at step S1 is negative (NO), step S1 is repeated. Meanwhile, if the judgement at step S1 is affirmative (YES), step S1 is followed by step S2 at which the rapid and slow deflation valves 14, 16 are closed and the electric pump 18 is driven, so as to inflate the cuff 10, namely, increase cuff pressure Pc.

Figure 3:
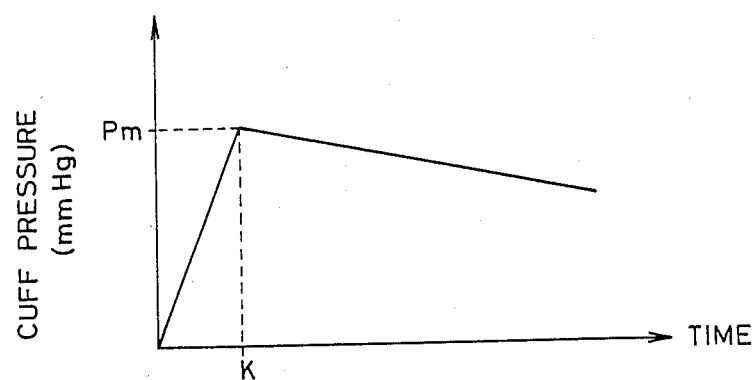
FIG. 3 is a graph showing an increase and a decrease in cuff pressure as an inflatable cuff of the apparatus of FIG. 1 is inflated and deflated, respectively.

At the following step S3 it is judged whether or not cuff pressure Pc has been increased to an upper target level Pm. Upper target level Pm is predetermined to be sufficiently higher than estimated maximum blood pressure of the subject, for example 180 mmHg. Steps S2 and S3 are repeated until cuff pressure Pc reaches upper target level Pm. If cuff pressure Pc has reached upper target pressure Pm, step S3 is followed by step S4 at which the electric pump 18 is stopped, and at the following step S5 the slow deflation valve 16 is opened. Thus, the cuff 10 is slowly deflated, namely, cuff pressure Pc is slowly decreased. The time of beginning of the slow cuff deflation is indicated at point K in the graph of FIG. 3. A resistance of the slow deflation valve 16 against fluid flow therethrough is predetermined such that, when the valve 16 is opened, cuff pressure Pc is decreased at the rate of 3 to 4 mmHg/sec, for example, which rate is appropriate to effect blood pressure measurement.

Figure 5:
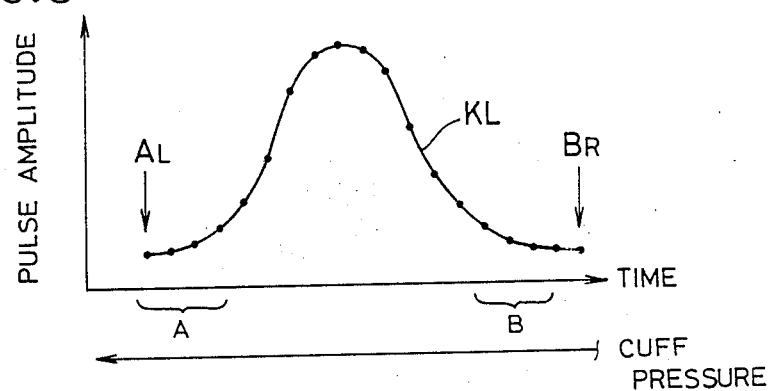
FIG. 5 is a graph showing a blood pressure evaluation curve utilized in the apparatus of FIG. 1.

At the following step S6 it is judged whether or not a pulse of the pulse wave has been detected, namely, whether or not pulse wave signal SPo representing a pulse of the pulse wave is present at the CPU 28. Each time the judgement at step S6 is affirmative, namely, each time a pulse of the pulse wave is detected, step S6 is followed by step S7 at which an amplitude of the detected pulse is stored in the RAM 34 together with the time of detection of the pulse and cuff pressure at the time of the detection. The pulse amplitude and the cuff pressure constitute a set of point data representing the detected pulse. As cuff pressure Pc is slowly decreased, a multiplicity of pulses of the pulse wave are detected, and the corresponding number of sets of point data are prepared and stored. Based on each set of point data, a point is plotted in a two-dimensional table defined by an axis of abscissa indicative of cuff pressure (or time) and an axis of ordinate indicative of pulse amplitude, as shown in FIG. 5. A blood pressure evaluation curve KL is obtained by connecting the points plotted in the two-dimensional table of FIG. 5. In the present embodiment, step S7 stored in the form of software program in the ROM 32 and the CPU 28 and the RAM 34 for effecting step S7, serve as the means for preparing sets of point data and plotting points based on the sets of point data.

At the following step S8 it is judged whether or not cuff pressure Pc has been decreased to a lower target level Pn, for example 40 mmHg, which is predetermined to be sufficiently lower than estimated minimum blood pressure of the subject. Steps S6 and S7 are repeated to consecutively detect pulses of the pulse wave, prepare sets of point data and plot points in the two-dimensional table, until the judgement at step S8 is turned affirmative. Cuff pressure Pc continues to be higher than lower target level Pn for a time since cuff pressure Pc is slowly decreased. Accordingly, the judgement at step S8 continues to be negative during that time. Thus, while cuff pressure Pc is slowly decreased from upper pressure level Pm to lower pressure level Pn, a sufficient number of sets of point data are prepared and the corresponding number of points are plotted in the two-dimensional table.

Once the judgement at step S8 is turned affirmative, step S8 is followed by step S9. Step S9 is a blood pressure determining routine in which maximum and minimum blood pressure of the subject is determined based on evaluation curve KL, namely, plotted points on evaluation curve KL. Step S9 is followed by step S10 at which the determined maximum and minimum blood pressure is displayed on the display device 38.

By reference to the flow chart of FIG. 4 there will be described in detail the blood pressure determining routine of step S9 of FIG. 2.

At step SR1 of FIG. 4 a point group PG consisting of three consecutive points is selected from the plotted points on evaluation curve KL. In the present embodiment, point group PG1 selected at a first cycle of the routine, is constituted by three consecutive points plotted at a lefthand-end portion A of evaluation curve KL in the graph of FIG. 5, such that the three points include point $A_L$ at the end of lefthand end portion A of curve KL. At a second cycle, is used point group PG2 consisting of three consecutive points which are shifted rightward by one point from the three points of point group PG1 used at the first cycle. More specifically described, point group PG2 used at the second cycle does not include lefthand end point $A_L$, and consists of the three consecutive points plotted following lefthand-end point $A_L$ as cuff pressure Pc is decreased. Point group PG is constituted in the same manner as described above at each of the following cycles of the routine. Thus, while being constituted by three consecutive points at each cycle, point group PG is shifted rightward along evaluation curve KL by one point at each cycle. Based on points plotted at lefthand-end portion A of evaluation curve KL, maximum blood pressure is determined (as described below). Similarly, minimum blood pressure is determined based on points plotted at a righthand-end portion B of evaluation curve KL, after the determination of the maximum blood pressure. In the case of determining minimum blood pressure, at a first cycle of the blood pressure determining routine of FIG. 4, a point group is constituted by three consecutive points plotted at righthand-end portion B of evaluation curve KL, such that the three points include point $B_R$ at the end of righthand end portion B. At the following cycle, is used a pulse group consisting of three consecutive pulses which are shifted leftward by one point from the three points of the point group used at the preceding cycle, namely, three points plotted preceding righthand-end point $B_R$ as cuff pressure Pc is decreased.

Step SR1 is followed by step SR2 at which a regression line RL1 is determined regarding the three consecutive points of point group PG2. More specifically described, regression RL1 is determined regarding the three consecutive points consisting of a "new" point following the three points of point group PG1 selected at step SR1 and the two points out of the three points of point group PG1 which two points are adjacent to the "new" point. The manner in which maximum blood pressure is determined, will be described by reference to the graph of FIG. 6. The graph includes four points P1, P2, P3, P4 plotted at lefthand end portion A of evaluation curve KL of FIG. 5, but point P1 is not lefthand end point $A_L$. Provided that point group PG1 is selected at step SR1 so as to consist of three points P1, P2, P3, regression line RL1 is determined at step SR2 regarding point group PG2 consisting of three points P2, P3, P4.

Generally, regression line RL of three points of point group PG is expressed by the following linear function (1):

$$Y = a \cdot X + b \quad (1),$$

wherein
X: cuff pressure (or time),
Y: pulse amplitude,
a: constant (slope of line RL), and
b: constant (y intercept of line RL).

Constants a, b are calculated by the following formulas (2) and (3):

$$a = \frac{\Sigma(x - \bar{x})(y - \bar{y})}{\Sigma(x - \bar{x})} \quad (2)$$

-continued $$b = \bar{y} - a\bar{x} \quad (3)$$

wherein
x, y: x and y coordinates of each of three points of point group PG, and
$\bar{x}, \bar{y}$: averages of x and y coordinates of three points of point group PG.

Thus, in the present embodiment, step SR1 stored in the ROM 32 and the CPU 28 and the RAM 34 for effecting step SR1, serve as the means for selecting the predetermined number of consecutive points from the plotted points, and step SR2 stored in the ROM 32 and the CPU 28 and the RAM 34 for effecting step SR2, serve as the means for determining a regression line of the selected consecutive points.

At the following step SR3, first, a standard deviation of points P1, P2, P3 of point group PG1 is calculated by the following formula (4):

$$s = \sqrt{\frac{\Sigma(y - \bar{y})^2 - a \cdot \Sigma(x - \bar{x})(y - \bar{y})}{n - 2}} \quad (4)$$

wherein
n: number of points of point group PG (three in the present embodiment).

Next, is determined a prediction interval PIT1 regarding point P4 ($x_k$, $y_4$) which is plotted adjacent to point P3, namely, plotted following point P3 when cuff pressure Pc is decreased. Prediction interval PIT1 is determined based on standard deviation s, and regression line RL0 determined at the preceding cycle of the blood pressure determining routine of FIG. 4. Prediction interval PIT1 regarding point P4 is defined by an upper and a lower limit thereof which are expressed as follows:

$$a \cdot x_k + b + t_{\alpha/2} \cdot s \cdot \quad (5)$$

$$\sqrt{1 + \frac{1}{n} + \frac{(x - \bar{x})^2}{\Sigma(x - \bar{x})^2} \quad \frac{(x_k - \bar{x})^2}{\Sigma(x - \bar{x})^2}}$$

wherein
t: value from t-Destribution Table, and
α: significance level.

Regarding a predetermined number (n) of samples the value of t is determined from a t-Distribution Table (also known as a Student's t Table), a standard reference found in most statistics textbooks, by locating the intersection of the row (column) corresponding to the degree of freedom (n−2) with the column (row) corresponding to the significance level (α).

Figure 6:
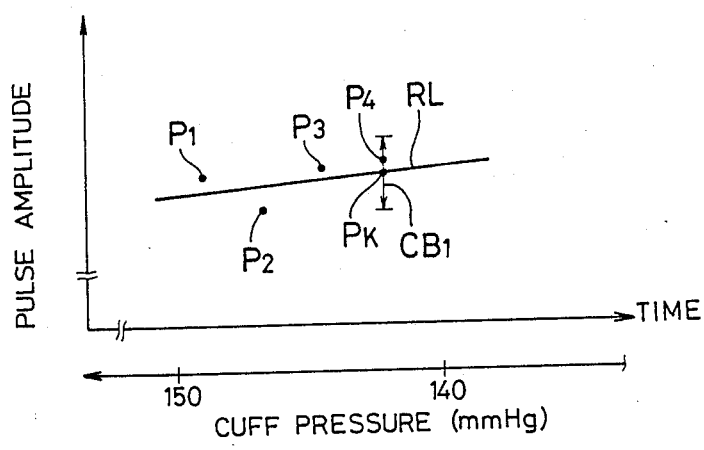
FIGS. 6 and 7 are graphs illustrating prediction intervals used for determining maximum and minimum blood pressure in the apparatus of FIG. 1, respectively.

Prediction interval PIT1 determined regarding P4 ($x_k$, $y_4$) is indicated at line segment CB1 in the graph of FIG. 6. Point P4 is plotted with a statistically high probability inside segment CB1. Point Pk ($x_k$, $a \cdot x_k + b$) on regression line RL is a middle point of segment CB1. If significance value α is 0.05, segment CB1 is a 95 percent confidence interval inside which point P4 is plotted with a 95 percent probability. In the present embodiment, step SR3 stored in the ROM 32 and the CPU 28 and the RAM 34 for effecting step SR3, serve as the means for determining the at least one prediction interval regarding the at least one point adjacent to the selected consecutive points.

Step SR3 is followed by step SR4 at which it is judged whether or not point P4 plotted following points P1, P2, P3 of pulse group PG1 selected at step SR1, is plotted inside prediction interval PIT1 determined at step SR3, namely, inside line segment CB1. At early cycles of the routine, points are plotted inside prediction intervals determined regarding the points, and the judgement at step SR4 continues to be affirmative for a time. Thus, steps SR1 through SR3 are repeated.

Meanwhile, if the judgement at step SR4 is turned negative, namely, if a point is plotted outside a prediction interval determined regarding the point at step SR3, step SR4 is followed by step SR5 at which it is judged each of three consecutive points is plotted outside a corresponding one of three prediction intervals. At the cycle in which the judgement at step SR4 has just been turned negative, the judgement at step SR5 is naturally negative. Accordingly, steps SR1 through SR4 are repeated at the following cycle. Specifically, at step SR1 a new pulse group is selected, a regression line for the next cycle is determined, a prediction interval is determined based on a regression line determined at the preceding cycle, and it is judged whether or not a point following the three points of the new pulse group is plotted inside the determined prediction interval.

Figure 7:
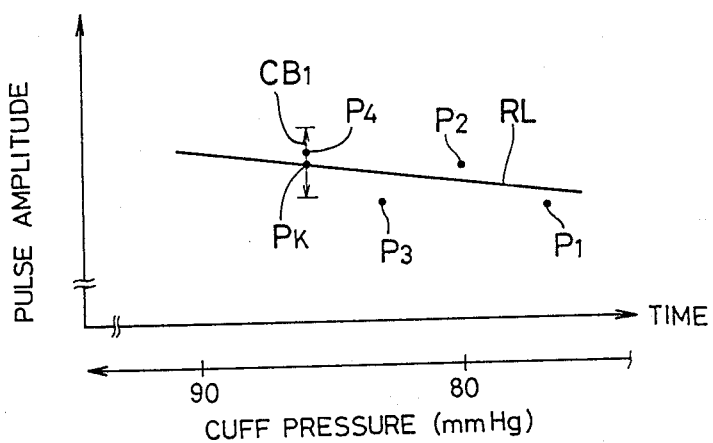

If the judgement at step SR5 is turned affirmative, namely, three consecutive points are plotted outside the corresponding three prediction intervals determined at the corresponding three consecutive cycles, step SR5 is followed by step SR6 at which maximum blood pressure is determined based on a selected one of the three consecutive points plotted outside the correponding three prediction intervals. It is experimentally determined which point of the three points is suitable to be selected. For example, a middle point of the three points is selected. The selected point is handled as a rising point of blood pressure evaluation curve KL, and cuff pressure represented by the rising point is determined as maximum blood pressure of the subject. Thus, maximum blood pressure is determined based on points plotted at lefthand end portion A of evaluation curve KL. Similarly, minimum blood pressure is determined based on a rising point selected from points P1, P2, P3, P4, . . . plotted in the graph of FIG. 7 which points correspond to points plotted at righthand end portion B of evaluation curve KL of FIG. 5. In the present embodiment, steps SR4 through SR6 stored in the ROM 32 and the CPU 28 and the RAM 34 for effecting those steps, serve as the means for determining blood pressure of the subject.

As is apparent from the foregoing, in the present embodiment, three consecutive points are selected from a multiplicity of points on a blood pressure evaluation curve, and a regression line of the selected three points is determined. The thus determined regression line represents an overall varying or dispersing tendency of the selected three points. Further, a prediction interval is determined regarding a point adjacent to the selected three points, based on the regression line and the selected three points. With a statistically (i.e., significantly) high probability, the point in question is plotted inside the prediction interval. Accordingly, if the point in question is plotted outside the predition interval, the point is treated as a rising point of the evaluation curve based on which maximum or minimum blood pressure is determined. Stated differently, if the point in question has statistically the same varying dispersing tendency as that of the selected three points, the point is plotted inside the prediction interval. Accordingly, if the point in question is plotted outside the prediction interval, it is statistically estimated that the point reflects a particular cause other than statistically predicted dispersion or variance. Thus, in the present embodiment, a rising point of the blood pressure evaluation curve is accurately selected, and maximum or minimum blood pressure is accurately determined based on the rising point.

Figure 8:
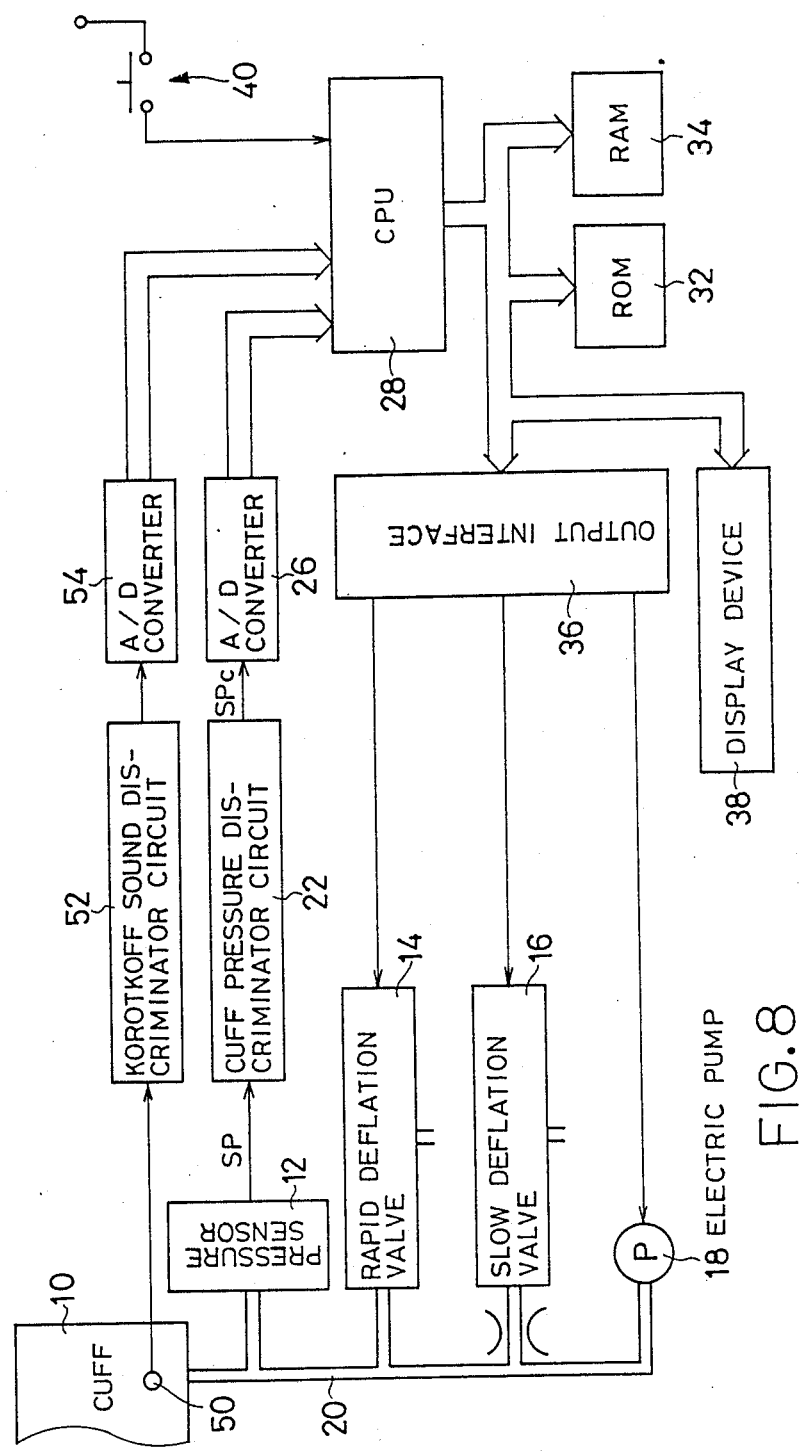
FIG. 8 is a view corresponding to FIG. 1, showing another blood pressure measuring apparatus embodying the invention.

Referring next to FIG. 8 there is illustrated another blood pressure measuring apparatus embodying the present invention. The same reference numerals as used in FIG. 1 are used to designate corresponding elements or parts of the instant apparatus, and repetitive description of those elements or parts will be omitted.

As shown in FIG. 8, the instant apparatus includes a microphone for collecting Korotkoff sounds, and generating electric signal representing the collected Korotkoff sounds. The Korotkoff sounds are produced from a subject synchronously with heartbeat of the subject, by pressing a body portion of the subject with an inflatable cuff 10. The apparatus further includes a Korotkoff sound discriminator circuit 52 including a band-pass filter which selectively transmits signals in a specific frequency band corresponding to the frequency range of the Korotkoff sounds. Signals transmitted through the discriminator circuit 52 are supplied to a CPU 28 via an A/D converter 54.

Figure 9:
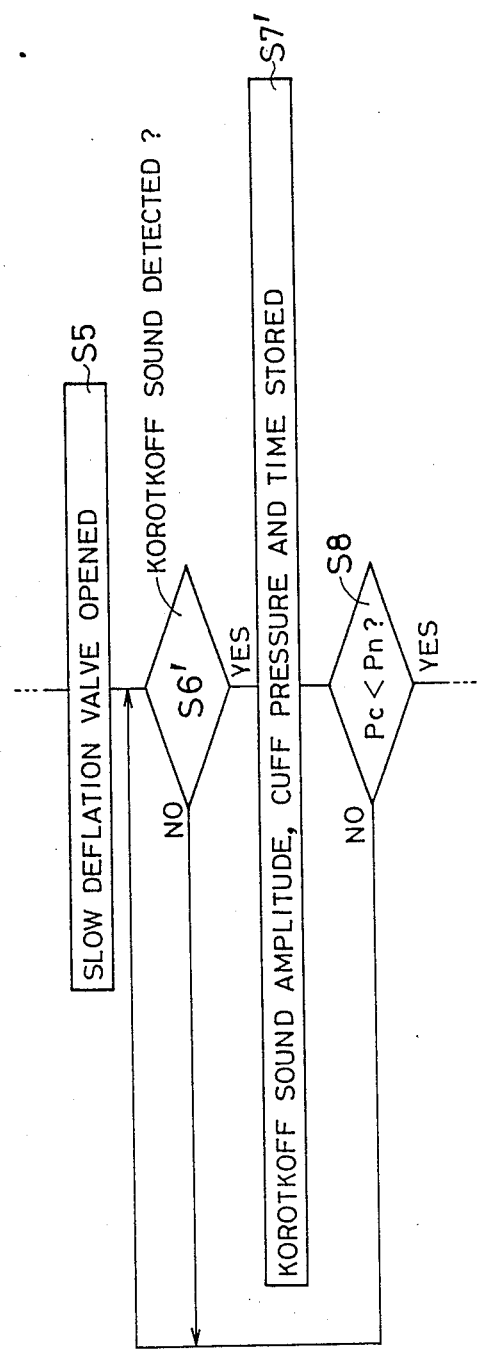
FIG. 9 is a flow chart illustrating a portion of the operation of the apparatus of FIG. 8.

The instant apparatus is operated to measure blood pressure, according to the same flow charts as those of FIGS. 2 and 4, except that steps S6 and S7 of FIG. 2 are replaced with steps S6' and S7' of FIG. 9 for the instant apparatus. Specifically, at step S6' it is judged whether or not a Korotkoff sound has been detected, and at step S7' an amplitude of the detected Korotkoff sound is stored together with the time of detection of the Korotkoff sound and cuff pressure at the time of the detection.

The instant apparatus provides the same advantages as those of the apparatus of FIG. 1. For example, a pair of rising points are selected from a blood pressure evaluation curve, and maximum and minimum blood pressure are determined based on the selected rising points with satisfactory accuracy.

Figure 10:
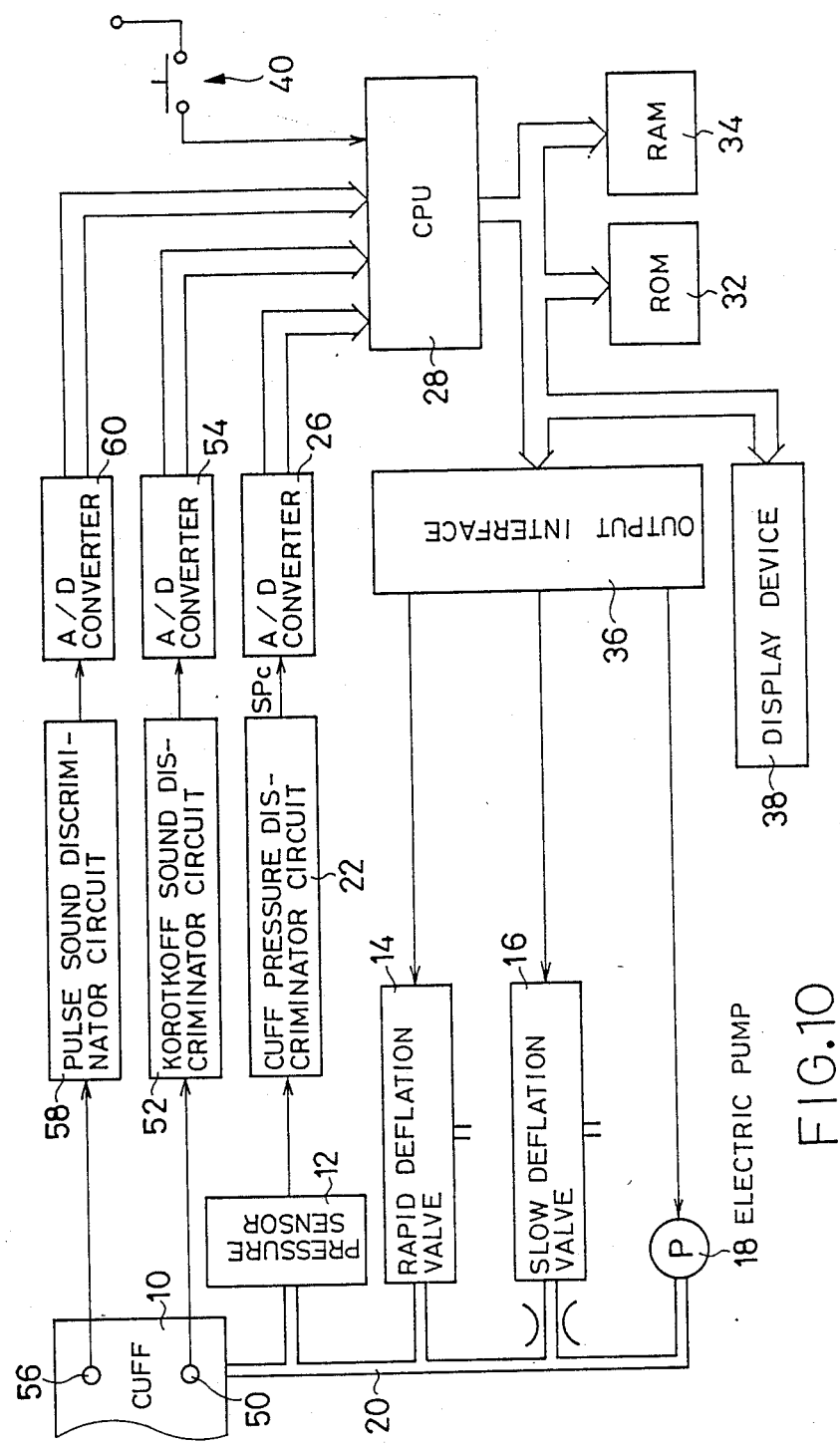
FIG. 10 is a view corresponding to FIGS. 1 and 8, showing yet another blood pressure measuring apparatus embodying the invention.

Referring further to FIG. 10 there is shown yet another blood pressure measuring apparatus embodying the present invention. The present apparatus is generally similar to the apparatus of FIG. 8, and additionally includes another microphone 56 which is set on an upstream side of an inflatable cuff 10 along an arterial vessel extending in an upper arm around which the cuff 10 is wound. The microphone 56 collects pulse sounds produced from the arterial vessel synchronously with heartbeat of the subject, and generates electric signal representing the collected pulse sounds, to a pulse sound discriminator circuit 58. The circuit 58 discriminates, from signal supplied from the microphone 56, a signal component corresponding to the pulse sounds. The signal component transmitted through the circuit 58 is supplied to a CPU 28 via an A/D converter 60.

The present apparatus is operated to determine blood pressure, according to the flow charts of FIGS. 2 and 4, except that steps S6 and S7 of FIG. 2 are replaced with steps SP1 through SP6 of FIG. 11 in the present apparatus. Specifically, at step SP1 it is judged whether or not a pulse sound has been detected through the upper microphone 56 set on the upstream side of the cuff 10. If the judgement at step SP1 is affirmative, step SP1 is followed by step SP2 at which the time of detection of the pulse sound is stored. Step SP2 is followed by step SP3 at which it is judged whether or not a Korotkoff sound has been detected through a microphone 50 set on a downstream side of the cuff 10. If the judgement at step SP3 is affirmative, at the following step SP4 an amplitude of the detected Korotkoff sound is stored together with the time of detection of the Korotkoff sound and cuff pressure at the time of the detection.

Step SP4 is followed by step SP5 at which is calculated a time difference between the time of detection of the pulse sound on the upstream side of the cuff 10 and the time of detection of the Korotkoff sound on the downstream side of the cuff 10. At the following step SP6 a set of product data is prepared by multiplying the time difference by the amplitude of the Korotkoff sound. While cuff pressure is slowly decreased, a multiplicity of sets of product data are prepared and a blood pressure evaluation curve is drawn based on the prepared product data. Similar to the preceding two apparatus, the present apparatus is capable of determining blood pressure with satisfactory accuracy.

While the present invention has been described in its presently preferred embodiments, the invention may be embodied with various modifications.

For example, while in the illustrated embodiments of FIGS. 1, 8, 10 maximum and minimum blood pressure is determined based on a pair of rising points selected from a blood pressure evaluation curve obtained as cuff pressure is slowly decreased, it is possible to obtain a blood pressure evaluation curve as cuff pressure is slowly increased and determined minimum and maximum blood pressure based on a pair of rising points selected from the thus obtained evaluation curve.

Although in the illustrated embodiments rising points are not selected from a blood pressure evaluation curve until all the points are plotted, namely, until cuff pressure is decreased to lower target level Pn, it is possible that, each time a point is plotted, the algorithm for selecting a rising point is effected. In this case, one of maximum and minimum blood pressure is earlier determined and displayed than the other. Specifically, in the case where a blood pressure evaluation curve is obtained as cuff pressure is decreased, maximum blood pressure is earlier determined and displayed than minimum blood pressure. On the other hand, in the case where an evaluation curve is obtained as cuff pressure is increased, minimum blood pressure is earlier determined and displayed than maximum blood pressure.

While in the illustrated embodiments a point group is constituted by three consecutive points, it is possible that the group point be constituted by four or more consecutive points selected from points on a blood pressure evaluation curve. Alternatively, it is possible to constitute point groups by a progressively increasing number of points, such that at a first cycle of the routine of FIG. 4 point group PG1 is constituted by three points, at the following cycle point group PG2 is constituted by four points, at the next cycle point group PG3 is constituted by five points . . .

Although in the illustrated embodiments both maximum and minimum blood pressure is determined based on a pair of rising points selected from a blood pressure evaluation curve, it is possible to adapt any of the three apparatus to determine and display only one of maximum and minimum blood pressure. In this case, the other blood pressure may be determined by a known blood pressure determining method.

It is to be understood that the present invention may be embodied with other modifications, changes and improvements that may occur to those skilled in the art without departing from the scope and spirit of the invention as defined in the appended claims.

What is claimed is:

1. A method of determining a blood pressure of a subject based on heartbeat-synchronous pulses which are produced from the subject by pressing a body portion of the subject with an inflatable cuff, the method comprising the steps of:

detecting said heartbeat-synchronous pulses as pressure in said cuff is varied, preparing plural sets of point data each of which represents a pressure of said cuff at the time of detection of a corresponding one of said pulses and a magnitude of said corresponding one pulse, plotting, based on the prepared plural sets of point data, a plurality of points in a two-dimensional table defined by a first axis indicative of said pressure of the cuff and a second axis indicative of said magnitude of the pulses, selecting a predetemined number of consecutive points from the plotted points such that said predetermined number is not less than three, determining a regression line of the selected consecutive points, statistically determining, based on the determined regression line, at least one prediction interval regarding at least one point plotted adjacent to said selected consecutive points, such that each of said at least one point is plotted with a statistically high probability inside a corresponding one of said at least one prediction interval, and determining a blood pressure of said subject based on said at least one point, if said each of the at least one point is plotted outside said corresponding one of the at least one prediction interval.

2. The method as set forth in claim 1, further comprising the steps of connecting said plotted points so as to obtain an evaluation curve, and determing, as a rising point of said evaluation curve, one of said at least one point if said each of the at least one point is plotted outside said corresponding one of the at least one prediction interval, a pressure of said cuff represented by said rising point being determined as said blood pressure of the subject.

3. The method as set forth in claim 1, wherein said at least one prediction interval consists of three prediction intervals determined regarding three consecutive points adjacent to said selected consecutive points, a pressure of said cuff represented by one of said three consecutive points being determined as said blood pressure of the subject.

4. The method as set forth in claim 1, wherein said heartbeat-synchronous pulses consist of pulses of pulse wave transmitted to said inflatable cuff synchronously with heartbeat of the subject.

5. The method as set forth in claim 1, wherein said heartbeat-synchronous pulses consist of Korotkoff sounds produced from said body portion of said subject synchronously with heartbeat of the subject.

6. The method as set forth in claim 1, wherein the step of detecting said heartbeat-synchronous pulses is effected as said pressure of the inflatable cuff is decreased.

7. The method as set forth in claim 1, wherein the step of detecting said heartbeat-synchronous pulses is effected as said pressure of the inflatable cuff is increased.

8. The method as set forth in claim 6, wherein the step of determining said blood pressure consists of at least one of determining a maximum blood pressure of said subject based on said at least one point following the selected consecutive points, and determining a minimum blood pressure of said subject based on said at least one point preceding the selected consecutive points different from the selected points utilized in determining the maximum blood pressure.

9. The method as set forth in claim 7, wherein the step of determining said blood pressure consists of at least one of determining a minimum blood pressure of said subject based on said at least one point plotted following the selected consecutive points, and determining a maximum blood pressure of said subject based on said at least one point preceding the selected consecutive points different from the selected points utilized in determining the minimum blood pressure.

10. An apparatus for determining a blood pressure of a subject based on heartbeat-synchronous pulses which are produced from the subject by pressing a body portion of the subject with an inflatable cuff, the apparatus comprising:

means for detecting said heartbeat-synchronous pulses as pressure in said cuff is varied;

means for preparing plural sets of point data each of which represents a pressure of said cuff at the time of detection of a corresponding one of said pulses and a magnitude of said corresponding one pulse, and plotting, based on the prepared plural sets of point data, a plurality of points in a two-dimensional table defined by a first axis indicative of said pressure of the cuff and a second axis indicative of said magnitude of the pulses;

means for selecting a predetermined number of consecutive points from the plotted points such that said predetermined number is not less than three, and means for determining a regression line of the selected consecutive points;

means for statistically determining, based on the determined regression line, at least one prediction interval regarding at least one point adjacent to said selected consecutive points, such that each of said at least one point is plotted with a statistically high probability inside a corresponding one of said at least one prediction interval; and means for determining a blood pressure of said subject based on said at least one point, if said each of the at least one point is plotted outside said corresponding one of the at least one prediction interval.

11. The apparatus as set forth in claim 10, wherein said at least one prediction interval consists of three prediction intervals determined regarding three consecutive points adjacent to said selected consecutive points, a pressure of said cuff represented by one of said three consecutive points being determined as said blood pressure of the subject.

12. The apparatus as set forth in claim 10, wherein said regression line is expressed by the following equation:

$$Y = aX + b,$$

wherein
X: pressure of said cuff,
Y: magnitude of said pulses,
a: slope (constant);

$$a = \frac{\Sigma(x - \bar{x})(y - \bar{y})}{\Sigma(x - \bar{x})}$$

b: y intercept (constant);

$$b = \bar{y} - a\bar{x}$$

x: pressure of said cuff represented by each of said selected consecutive points,
y: magnitude of said pulses represented by each of said selected consecutive points,
$\bar{x}$: average of the pressures of said cuff represented by said selected consecutive points, and
$\bar{y}$: average of the magnitudes of said pulses represented by said selected consecutive points.

13. The apparatus as set forth in claim 12, wherein the prediction interval determined regarding a point P plotted adjacent to said selected consecutive points is defined by an upper and a lower limit thereof which are expressed as follows:

$$a \cdot x_k + b \pm t_{\alpha/2} \cdot s \cdot \sqrt{1 + \frac{1}{n} + \frac{(x_k - \bar{x})^2}{\Sigma(x - \bar{x})^2}},$$

wherein
$x_k$ is x coordinate of said point P,
s is a standard deviation of said selected consecutive points,
n is a said predetermined number,
t is a value from t-Distribution Table, and
α is significance level,
the value of said t being known from t-Distribution table according to a value of said α and a degree of freedom given by (n−2).

* * * * *